US00PP21879P3

(12) United States Plant Patent

Poulter et al.

(10) Patent No.: US PP21,879 P3

(45) Date of Patent: Apr. 19, 2011

(54) *COSMOS* PLANT NAMED '3013/01'

(50) Latin Name: *Cosmos×atrosanguineus*
Varietal Denomination: 3013/01

(76) Inventors: Russell Poulter, Dunedin (NZ); Keith Hammett, Auckland (NZ)

( * ) Notice: Subject to any disclaimer, the term of this patent is extended or adjusted under 35 U.S.C. 154(b) by 0 days.

(21) Appl. No.: 12/587,072

(22) Filed: Sep. 30, 2009

(65) Prior Publication Data

US 2010/0083412 P1 Apr. 1, 2010

(51) Int. Cl.
*A01H 5/00* (2006.01)

(52) U.S. Cl. ..... Plt./418

(58) Field of Classification Search ..... Plt./263, Plt./418

See application file for complete search history.

(56) References Cited

U.S. PATENT DOCUMENTS

PP19,223 P2 * 9/2008 Takayoshi ..... Plt./418

* cited by examiner

*Primary Examiner* — Susan B McCormick Ewoldt

(57) ABSTRACT

A new cultivar of *Cosmos* plant named '3013/01' which exhibits a compact habit and which bears dark maroon colored flowers from late spring through late summer. In combination these traits set '3013/01' apart from all other existing varieties of *Cosmos* known to the inventor.

2 Drawing Sheets

Genus: *Cosmos.*
Species: *×atrosanguineus.*
Denomination: '3013/01'.

BACKGROUND OF THE INVENTION

This application claims the benefit of priority under 35 U.S.C. 119(f) of the application for a grant of New Zealand Plant Breeders Rights which was filed for the instant plant variety on Oct. 1, 2008, Application Number HOM254.

The present invention relates to a new and distinct cultivar of *Cosmos,* also commonly known as chocolate *cosmos,* that is grown for use as a flowering plant for pots and containers and for planting in the garden and landscape. The new cultivar is known botanically as *Cosmos×atrosanguineus* and will be referred to hereinafter by the cultivar name '3013/01'.

'3013/01' is a complex hybrid plant that is the product of a breeding program which is conducted jointly by the inventors. Pollinations are carried out in a cultivated area in Dunedin, New Zealand and evaluations and selections are carried out in Auckland, New Zealand.

'3013/01' resulted from the open pollination between one seedling which had been raised from the seed strain of *Cosmos* which is sold commercially as *Cosmos* Pinot Noir as female parent plant and an unknown, unreleased seedling which is no longer retained by the inventors as male parent plant. Whereas plants raised as seedlings from the Pinot Noir strain are invariably sparse in habit, same-age plants of '3013/01' are well branched at the base and thereby more dense in habit. The inventors are unable to recall the characteristics of the male parent plant.

The closest variety of *Cosmos* known to the inventor is *Cosmos* 'New Choco' (U.S. Plant Pat. No. 19,223). '3013/01' maintains a compact habit such that the width of a mature flowering one year old plant is approximately the same as its height, including the flowers. By comparison, 'New Choco' grows with an outwardly spreading habit such the width of a mature plants is approximately one and a half times greater than its height.

'3013/01' may also be compared with the variety *Cosmos* 'Chocamocha' (unpatented). Whereas the foliage of '3013/01' is mid-green in color, the foliage of 'Chocamocha' is silver-green in color. In addition, the flowers of '3013/01' are dark maroon in color whereas the flowers of 'Chocamocha' are lighter and redder in color.

Asexual reproduction of '3013/01' was first accomplished under the inventors' direction at a tissue culture laboratory in Auckland, New Zealand. The method of asexual propagation used was division by tissue culture. The inventors have grown out successive generations of plants resulting from the tissue culture and have determined that the characteristics of '3013/01' are stable and reproduced true to type in successive generations of asexual reproduction.

SUMMARY OF THE INVENTION

The following traits have been repeatedly observed and represent the characteristics of the new *Cosmos* cultivar '3013/01'. These traits in combination distinguish this cultivar from all other varieties of *Cosmos* known to the inventor. '3013/01' has not been tested under all possible conditions and phenotypic differences may be observed with variations in environmental, climatic and cultural conditions, however, without any variance in genotype.

1. *Cosmos* '3013/01' exhibits a compact habit.
2. *Cosmos* '3013/01' exhibits flowers that are dark maroon in color.
3. *Cosmos* '3013/01' blooms from late spring through late summer.
4. After one year of growth, *Cosmos* '3013/01' achieves a height (including flowers) of 0.5 m and a spread of 0.5 m.
5. *Cosmos* '3013/01' is a tender perennial which is hardy in USDA Hardiness Zone 8 and above.

BRIEF DESCRIPTION OF THE DRAWINGS

The accompanying color drawings illustrate the overall appearance of the new *Cosmos* variety '3013/01' showing colors as true as it is reasonably possible to obtain in colored reproductions of this type. Colors in the drawings may differ from the color values cited in the detailed botanical description, which accurately describe the actual colors of the new variety '3013/01'.

The drawing labeled as FIG. 1 depicts an entire flowering plant.

Figure 1:
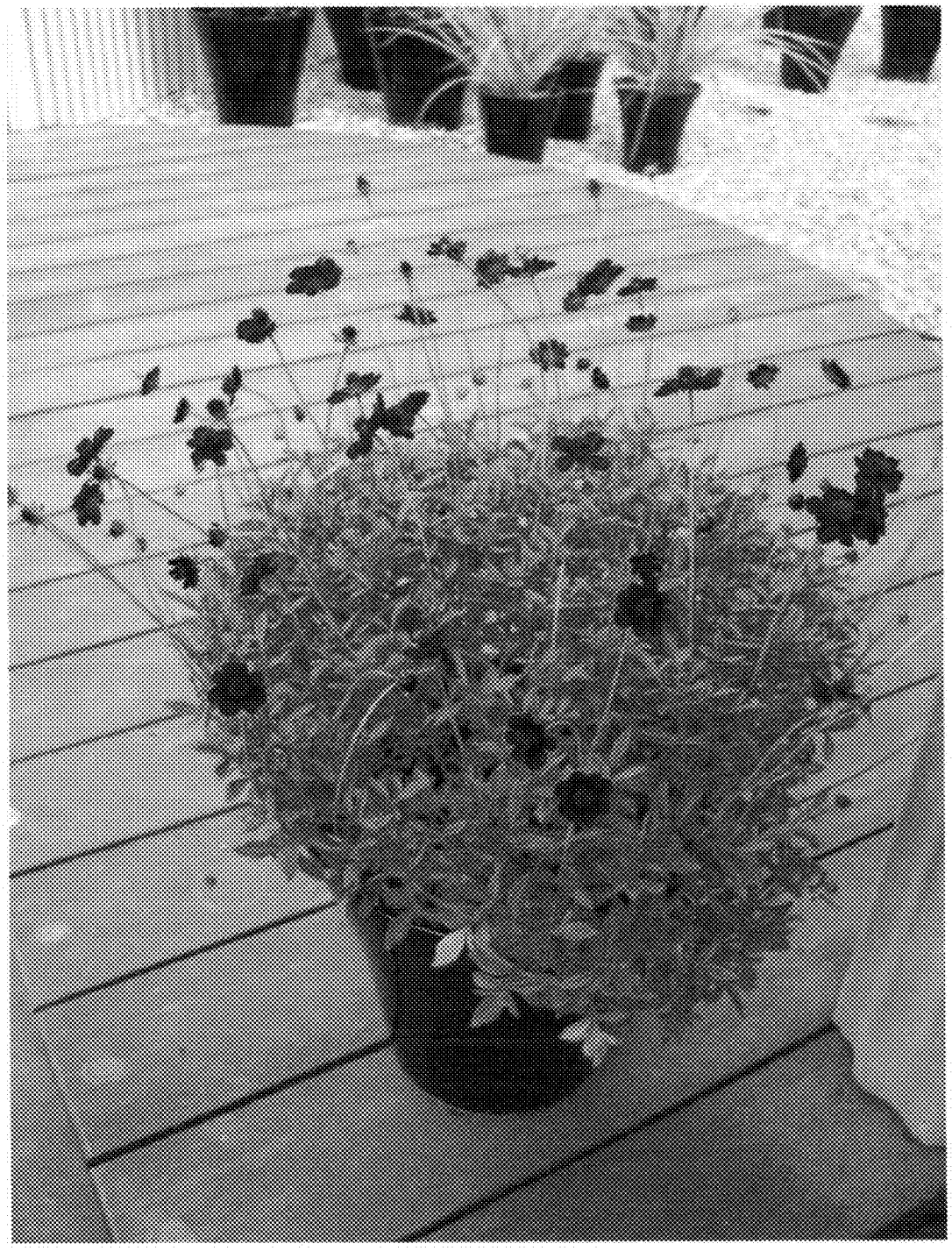
Figure 2:
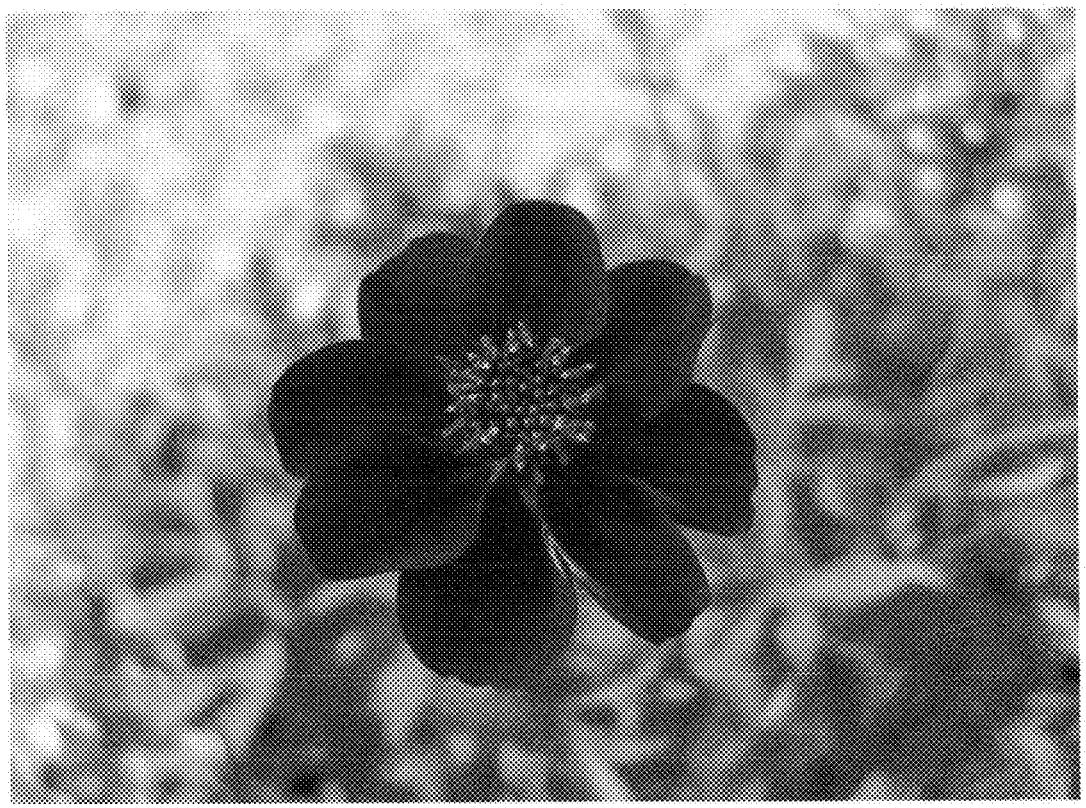

The drawing labeled as FIG. 2 depicts a close-up view of the flower.

Both drawings were made from one year old plants which have been grown in 1.5-litre containers in Auckland, New Zealand. No chemicals were used to treat the plants.

DETAILED BOTANICAL DESCRIPTION

The following is a detailed description of the new cultivar '3013/01'. Data was collected in summer in New Zealand from 1.5-litre container plants which had been grown out of doors in Auckland, New Zealand. The color determinations are in accordance with the 2001 edition of The Royal Horticultural Society Colour Chart, London, England, except where general color terms of ordinary dictionary significance are used. No chemicals were used to treat the plants. Growing conditions are typical to other *Cosmos*.

Botanical classification:
Family: Asteraceae
Genus: *Cosmos*
Species: ×*atrosanguineus*
Denomination: '3013/01'
Parentage:
- *Male parent.*—Unknown.
- *Female parent.*—*Cosmos* 'Pinot Noir' (unpatented).

Plant type: Flowering perennial.
Use of plant: As a flowering plant in containers, planters, pots and the garden and landscape.
Bloom period: Late spring through late summer.
Plant habit: Multiple stems arising from the tuber at ground level
Height of plant: 0.5 m at maturity
Width of plant: 0.5 m at maturity
Hardiness: USDA Hardiness Zone 8.
Root system: Initially fibrous, subsequently producing root tubers.
Branching: Basal branching and further branching from the axils of the lower leaves.
Propagation method: Tissue culture
Cultural requirements: Grow in full sun, in well drained and moderately fertile soil, keep well fertilized and watered.
Diseases and pests: No particular resistance or susceptibility to diseases and pests are known to the inventors.
Crop time: 3 months starting in the spring and 6 months starting in the fall.
Plant stem:
- *Shape.*—Cylindrical
- *Length* (*basal stems*).—0.3 m.
- *Diameter* (*basal stems*).—8 mm at base, 5 mm towards apex.
- *Length* (*axillary stems*).—0.2 m.
- *Diameter* (*axillary stems*).—4 mm-5 mm.
- *Surface texture* (*all stems*).—Sparely hirsute.
- *Color.*—Crimson, 187A.
- *Internode length* (*between nodes*).—30 mm-70 mm.

Leaf:
- *Type.*—Evergreen.
- *Shape.*—Pinnate.
- *Apex.*—Acute.
- *Base.*—Acuminate.
- *Venation.*—Pinnate.
- *Vein color.*—138A.
- *Margin.*—Entire.
- *Arrangement.*—Opposite.
- *Surface texture* (*upper surface*).—Smooth.
- *Surface texture* (*lower surface*).—Minutely Rugose.
- *Dimensions.*—Length: 110 mm to 150 mm. Width: 40 to 60 mm.
- *Color.*—Upper surface: 138A. Lower surface: 138C.
- *Attachment.*—Petiolate.
- *Petiole dimensions.*—Length: 50 mm-75 mm. Diameter: 2 mm-4 mm.
- *Petiole texture.*—Smooth.
- *Petiole color.*—138A.

Inflorescence:
- *Type.*—Capitulum.
- *Fragrance.*—Pleasant: reminiscent of chocolate.
- *Flowering season.*—Late spring through late summer.
- *Persistence of inflorescence on and off plant.*—7-10 days.
- *Quantity of inflorescences per plant at peak summer flowering.*—Many: approximately 25 flowers in bud to fully open.

Peduncles:
- *Length.*—40 mm-45 mm, diameter 2 mm.
- *Angle to stem.*—Vertical initially, arching away.
- *Strength.*—Wiry.
- *Texture.*—Smooth.
- *Color.*—Predominantly 138A with longitudinal striations of red 187B.

Buds:
- *Shape.*—Globose.
- *Dimensions.*—Length 9.5 mm, width 9.5 mm.
- *Color.*—138A.

Ray florets:
- *Arrangement.*—Single outer circle.
- *Length.*—15 mm-17 mm.
- *Width.*—12 mm-14 mm.
- *Apex.*—Truncate.
- *Base.*—Obtuse.
- *Margin.*—Entire.
- *Texture* (*upper surface*).—Puberulous.
- *Texture* (*lower surface*).—Puberulous, slight pubescence on veins.
- *Number of ray florets per inflorescence.*—6-8.
- *Color* (*both surfaces*).—Dark maroon, darker than 187A.

Disc florets:
- *Arrangement.*—Circular.
- *Shape.*—Tubular.
- *Length at anthesis.*—17 mm.
- *Width at anthesis.*—1.5 mm.
- *Apex.*—Divergent stigmas: top of tube 5-lobed, acute.
- *Base.*—Subtended directly from receptacle.
- *Margin.*—Smooth.
- *Texture, upper and lower surfaces of tube.*—Smooth.
- *Number of ray florets per inflorescence.*—6-8.
- *Color* (*both surfaces*).—Dark maroon, darker than 187A.

Reproductive organs:
- *Androecium.*—Present on disc florets only.
- *Anthers.*—Shape: Flattened cylinder, dehiscing on the inner surface only. Length: 4 mm-5 mm. Color: Dark maroon, darker than 187A.
- *Pollen.*—Copious, colored yellow 17A.
- *Gynoecium.*—Present on disc florets only.

*Pistil length.*—13 mm.
*Stigma shape.*—Divergent bifid curved.
*Stigma color.*—Dark maroon, darker than 187A.
*Style length.*—10 mm.
*Style color.*—Cream 157D at base, dark maroon at tip, darker than 187A.
*Ovary shape.*—Cylindrical, length 3 mm, width 0.75 mm.
*Ovary color.*—Cream 155D.
*Seed.*—Not Present.

It is claimed:

1. A new and distinct cultivar of *Cosmos* plant named '3013/01' as described and illustrated herein.

* * * * *